US007279275B2

(12) United States Patent
Pekosz et al.

(10) Patent No.: US 7,279,275 B2
(45) Date of Patent: Oct. 9, 2007

(54) METHODS AND COMPOSITIONS FOR DETECTION OF SEGMENTED NEGATIVE STRAND RNA VIRUSES

(75) Inventors: Andrew S. Pekosz, University City, MO (US); Paul D. Olivo, St. Louis, MO (US)

(73) Assignees: Washington University, St. Louis, MO (US); Apath, LLC, St. Louis, MO (US)

( * ) Notice: Subject to any disclaimer, the term of this patent is extended or adjusted under 35 U.S.C. 154(b) by 6 days.

(21) Appl. No.: 10/700,239

(22) Filed: Nov. 3, 2003

(65) Prior Publication Data

US 2005/0095583 A1    May 5, 2005

(51) Int. Cl.
  *C12Q 1/70* (2006.01)
  *C12Q 1/68* (2006.01)
  *C12P 19/34* (2006.01)
(52) U.S. Cl. .............................. 435/5; 435/6; 435/91.1
(58) Field of Classification Search .................. 435/4, 435/5, 6, 235.1, 69.1, 325, 320.1; 424/199.1, 424/209.1, 208.1; 514/44
See application file for complete search history.

(56) References Cited

U.S. PATENT DOCUMENTS

| 5,591,579 A | 1/1997 | Olivo et al. | |
|---|---|---|---|
| 5,851,757 A | 12/1998 | Olivo et al. | |
| 6,270,958 B1 * | 8/2001 | Olivo et al. | 435/5 |

OTHER PUBLICATIONS

Fodor et. al., "Rescue of Influenza A Virus from Recombinant DNA," Journal of Virology, Nov. 1999, vol. 73, No. 11: p. 9679-9682.*
Neumann et al., Virology 202: 477-479, 1994.*
Nakagawa et al., "The PB1 Subunit alone can catalyze cRNA synthesis, and the PA subunit in Addition to the PB1 Subunit Is Required for Viral RNA synthesis in Replication of the Influenza Virus Genome," Journal of Virology, vol. 70, No. 9 (1996); 6390-4.*
Definition from Merriam-Webster Online Dictionary, 10th edition, indexed Mar. 15, 2003.*
Klumpp et al., "Roles of the influenza virus polymerase and nucleoprotein in forming a functional RNP structure," The EMBO Journal, vol. 16, No. 6, pp. 1248-1257 (1997).*
Lee et al., "Definition of the minimal viral components required for the initiation of unprimer RNA synthesis by influenza virus RNA polymerase," Nucleic Acids Research, vol. 30, No. 2, pp. 429-438 (2002).*

(Continued)

*Primary Examiner*—Bruce R. Campell
*Assistant Examiner*—M. Franco Salvoza
(74) *Attorney, Agent, or Firm*—Thompson Coburn LLP

(57) ABSTRACT

The present invention provides compositions and methods for the detection of the presence, absence, or quantity of a segmented negative strand RNA virus such as an influenza virus. A genetically engineered vertebrate cell comprising an artificial segment comprising a 5' UTR and a 3' UTR of a segmented negative strand RNA virus and an open reading frame of a reporter gene, preferably in an anti-sense orientation, is contacted with a biological specimen suspected of comprising a segmented negative strand virus. Infection of the cell with a segmented negative strand RNA virus results in expression of a polypeptide encoded by the reporter gene. A genetically engineered cell of the invention can also comprise a recombinant DNA encoding the artificial segment. The recombinant DNA can comprise a promoter for RNA Polymerase I for directing transcription of the artificial segment.

28 Claims, 5 Drawing Sheets

MAP OF PLASMID pHH21 NP UTR luciferase

OTHER PUBLICATIONS

Perales et al., "The Influenza Virus PB2 Polymerase Subunit Is Required for the Replication of Viral RNA," Journal of Virology, vol. 71, No. 2, pp. 1381-1385 (1997).*

Portela et al., "The influenza virus nucleoprotein: a multifunctional RNA-binding protein pivotal to virus replication," Journal of General Virology, 83, pp. 723-734 (2002).*

Szymkowiak et al,, "Rapid method for the characterization of 3' and 5' UTRs of influenza viruses," Journal of Virological Methods, 107, pp. 15-20 (Jan. 2003).*

Hoffmann et al., Proceedings of the National Academy of Sciences USA 97: 6108-6113, 2000.

Mikulasolva et al., Acta Virologica 44: 273-282, 2000.

Neumann et al., Proceedings of the National Academy of Sciences USA 96: 9345-9350, 1999.

Pekosz et al., Proceedings of the National Academy of Sciences USA 96: 8804-8806, 1999.

Zobel et al., Nucleic Acids Research 21: 3607-3614, 1993.

* cited by examiner

METHODS AND COMPOSITIONS FOR DETECTION OF SEGMENTED NEGATIVE STRAND RNA VIRUSES

FIELD

This application relates generally to the field of virology and, more particularly, to methods for detecting and quantifying a negative-strand segmented RNA virus in a biological specimen. This application also relates to cells modified for use in such methods.

BACKGROUND

Negative strand RNA viruses are the cause of numerous diseases in humans and animals. Detection and quantification of negative strand RNA viruses in biological specimens are thus of importance to both clinicians and researchers.

Negative strand RNA viruses can comprise segmented RNA or non-segmented RNA. In a non-segmented negative strand RNA virus, the entire viral genome is comprised by a single negative-sense RNA molecule, whereas in a segmented negative strand RNA virus, the viral genome is comprised by a plurality of negative-sense RNA segments. Among the segmented negative strand RNA viruses are the Arenaviridae, the Bunyaviridae and the Orthomyxoviridae, comprising two, three and six to eight segments, respectively. Each segment of vRNA comprises, in 5' to 3' order, a 5' untranslated region ("UTR"), at least one anti-sense open reading frame sequence encoding a viral polypeptide, and a 3' UTR. The UTRs are recognized by and/or bind to at least one protein involved with segmented negative strand RNA replication and/or gene expression, such as an RNA-dependent RNA polymerase. It is now generally accepted that expression of a protein encoded by a segment requires that the segment have precisely defined 5' and 3' terminal sequences.

U.S. Pat. Nos. 5,591,579 and 5,851,757, to Olivo et al. disclose cell lines and methods for detecting the presence of non-segmented RNA viruses in biological specimens. The cell lines are transformed with a DNA molecule that comprises a promoter capable of recognition by a cellular DNA-dependent RNA polymerase. The promoter, which is capable of directing the transcription of a cDNA of a structurally defective RNA virus, is linked to a reporter cDNA. The RNA molecules transcribed by the DNA-dependent RNA polymerase are not capable of causing the translation of reporter cDNA unless an active related virus is provided that contributes certain trans-acting viral enzymes.

U.S. Pat. No. 6,270,958 to Olivo et al. discloses a diagnostic assay for detecting a non-segmented negative-strand RNA virus in a biological specimen. In the disclosed assay, a genetically engineered cell expresses a minigenome or miniantigenome of a negative strand RNA virus. The minigenome or miniantigenome comprises a reporter gene or its complement, and flanking sequences from viral RNA. The cell also comprises recombinant DNA sequences each comprising a promoter directing the expression of nucleocapsid protein of the virus. Expression of the reporter gene in these cell lines depends upon the presence of the nucleocapsid proteins as well as infection of the cell with the virus.

Because expression of a polypeptide encoded by a segment of a segmented negative strand RNA virus requires precisely defined 3' and 5' terminal sequences, investigators have exploited the biochemical properties of RNA polymerase I (Pol I) to investigate expression of cDNAs of segments of segmented negative strand RNA viruses. Pol I is believed to initiate and terminate transcription at precise nucleotide sequences. In this regard, Zobel et al., Nucleic Acids Research 21: 3607-3614, 1993, and Neumann et al., Virology 202: 477-479, 1994 generated recombinant DNA constructs comprising a promoter recognized by Pol I (a "Pol I promoter") derived from a mouse ribosomal RNA (rDNA) gene. The Pol I promoter in these recombinant DNA constructs directed transcription (presumably by Pol I) of an operably linked DNA sequence comprising a Pol I transcription start site, an influenza virus segment comprising a 5' untranslated region (UTR) of an influenza virus RNA segment, a sequence complementary to a chloramphenicol acetyltransferase (CAT) coding sequence (replacing a hemagglutinin cDNA), and a 3' UTR, as well as a transcription terminator sequence recognized by Pol I polymerase (a "Pol I terminator"). Cells infected with influenza virus that were transfected with this DNA construct expressed CAT activity, suggesting that a virus-encoded RNA-dependent RNA polymerase was able to use the Pol I transcript as a template, resulting in a translatable mRNA encoding an active CAT enzyme.

These and similar studies have led to complete production of influenza virus using recombinant DNAs comprising cDNAs of influenza virus segments. In this connection, Neumann et al., Proceedings of the National Academy of Sciences USA 96: 9345-9350, 1999, and Hoffmann et al., Proceedings of the National Academy of Sciences USA 97: 6108-6113, 2000 disclose "reverse genetics" DNA transfection systems for generation of influenza A viruses entirely from cloned cDNAs. In these studies, cells were transfected with a first series of plasmids, each plasmid comprising a DNA sequence comprising a Pol I promoter operably linked to a cDNA of a vRNA segment, as well as a second series of plasmids, each plasmid comprising a Pol II promoter operably linked to a cDNA encoding a viral protein. The viral proteins transcribed in this system included viral nucleoprotein (NP) and polymerase complex proteins (comprising proteins PA, PB1, and PB2).

SUMMARY OF THE INVENTION

The present invention encompasses compositions and methods for detecting or determining the presence, absence, or quantity of at least one segmented negative strand RNA virus in a biological specimen suspected of comprising the segmented negative strand RNA virus. The present invention also encompasses compositions and methods for screening anti-viral compounds active against a segmented negative strand RNA virus.

In one embodiment, the invention provides a genetically engineered vertebrate cell comprising a recombinant RNA molecule that comprises a reporter gene encoding a polypeptide. In preferred embodiments, the vertebrate cell can be a mammalian cell. In certain embodiments, a cell does not contain a viral RNA-dependent RNA polymerase of a segmented negative strand RNA virus for which the detection or determination of the presence, absence, or quantity is sought. Formation of a translatable mRNA comprising the reporter gene requires the introduction into the cell of an RNA-dependent RNA polymerase of the segmented negative strand virus.

Accordingly, in another embodiment, the invention provides a method for detecting or determining the presence, absence, or quantity of a segmented negative strand virus in a biological specimen suspected of comprising the segmented negative strand RNA virus. The method comprises contacting the biological specimen with the genetically engineered vertebrate cell comprising a recombinant RNA molecule as described supra, and detecting the absence, presence, or quantity of a polypeptide encoded by the reporter gene.

In another embodiment, the invention provides a genetically engineered vertebrate cell comprising a recombinant DNA molecule that comprises a reporter gene in which expression depends upon the presence in the cell of a viral RNA-dependent RNA polymerase of a segmented negative strand virus. Thus, the invention also provides an isolated recombinant DNA molecule that comprises a reporter gene in which expression in a cell comprising the DNA molecule depends upon the presence in the cell of a viral RNA-dependent RNA polymerase of a segmented negative strand virus.

Accordingly, in another embodiment, the invention provides another method for detecting or determining the presence, absence, or quantity of a segmented negative strand virus in a biological specimen suspected of comprising the segmented negative strand RNA virus. The method comprises contacting the biological specimen with the genetically engineered vertebrate cell comprising a recombinant DNA molecule as described supra, and detecting the absence, presence, or quantity of the polypeptide encoded by the reporter gene.

In another embodiment, the invention provides a genetically engineered vertebrate cell for detecting or determining the presence, absence, or quantity of a first segmented negative strand RNA virus and a second segmented negative strand RNA virus in a biological specimen. The cell of this embodiment comprises a first recombinant RNA molecule that comprises a first reporter gene in which expression depends upon the presence in the cell of a viral RNA of a first segmented negative strand RNA virus, and a second recombinant RNA molecule that comprises a second reporter gene in which expression depends upon the presence in the cell of a viral RNA of a second segmented negative strand RNA virus.

Accordingly, in another embodiment, the invention provides a method for detecting or determining the presence, absence, or quantity of a first segmented negative strand RNA virus and a second segmented negative strand RNA virus in a biological specimen. The method comprises contacting the biological specimen with a genetically engineered vertebrate cell, the cell comprising a first recombinant RNA molecule and a second recombinant RNA molecule as described supra, and detecting the absence, presence, or quantity of a first polypeptide encoded by the first reporter gene and the absence, presence, or quantity a second polypeptide encoded by the second reporter gene.

In another embodiment, the invention provides a genetically engineered vertebrate cell for detecting or determining the presence, absence, or quantity of a first segmented negative strand RNA virus and a second segmented negative strand RNA virus in a biological specimen. The cell of this embodiment comprises a first recombinant DNA molecule that comprises a first reporter gene in which expression depends upon the presence in the cell of a viral RNA of a first segmented negative strand RNA virus, and a second recombinant DNA molecule that comprises a second reporter gene in which expression depends upon the presence in the cell of a viral RNA of a second segmented negative strand RNA virus.

Accordingly, in another embodiment, the invention provides a method for detecting or determining the presence, absence, or quantity of a first segmented negative strand RNA virus and a second segmented negative strand RNA virus in a biological specimen. The method comprises contacting the biological specimen with a genetically engineered vertebrate cell, the cell comprising a first recombinant DNA molecule and a second recombinant DNA molecule as described supra, and detecting the absence, presence, or quantity of a first polypeptide encoded by the first reporter gene and the absence, presence, or quantity a second polypeptide encoded by the second reporter gene.

In yet another embodiment, the invention provides a method of determining a differential diagnosis between an infection of influenza A virus, influenza B virus, or neither virus in a biological specimen suspected of comprising an influenza virus. The method comprises contacting the biological specimen with a population of genetically engineered cells, wherein a substantial plurality of the genetically engineered cells comprise a recombinant RNA molecule that comprises at least one UTR of a segment of an influenza A virus, and a reporter gene. In this embodiment, reporter gene polypeptide expression depends upon the presence in the cell of a viral RNA-dependent RNA polymerase of an influenza A or influenza B virus. Quantitative analysis of reporter gene expression in the cells reveals the viral content of the biological specimen: a cell population contacted with a biological specimen comprising influenza A virus produces an amount of reporter gene product substantially greater than that of an uninfected control culture, whereas a cell population contacted with a biological specimen comprising influenza B virus produces an amount of reporter gene product that is slightly greater than that of an uninfected control culture, and whereas a cell population contacted with a biological specimen comprising no pathogen virus, or a pathogen other than influenza A virus or influenza B virus, produces an amount of reporter gene product not significantly greater than that of an uninfected control culture.

In another embodiment, the invention provides a kit comprising packaging or instructions, and an isolated recombinant DNA molecule, the isolated recombinant DNA molecule comprising a reporter gene in which protein expression depends upon the presence in the cell of a viral RNA-dependent RNA polymerase of a segmented negative strand virus.

In another embodiment, the invention provides a quantitative screen for anti-viral drugs directed against a segmented negative strand RNA virus. The method comprises contacting a candidate anti-viral compound with a genetically engineered cell comprising an artificial segment comprising a reporter gene as described supra, wherein the cell also comprises a viral protein complex comprising a viral RNA-dependent RNA polymerase, and measuring expression levels of the reporter gene polypeptide. In certain embodiments, the protein complex can be provided by expression of a plurality of plasmids comprised by the cell, each plasmid encoding at least one polypeptide comprising the protein complex. In other embodiments, the protein complex can be provided by infection of the cell by a segmented negative strand RNA virus. Efficacy of a candidate anti-viral compound is determined by comparing the expression level of the reporter gene polypeptide in a cell (or population of cells) contacted with the compound to that of a control a cell or cell population not contacted with the compound.

In another embodiment, the invention provides a quantitative screen for anti-viral drugs directed against a segmented negative strand RNA virus. The method comprises contacting a candidate anti-viral compound with a cell infected with the virus; and detecting the presence, absence, or quantity of virus produced by the cell. The detecting comprises contacting a genetically engineered cell (or population of cells) comprising an artificial segment comprising a reporter gene, as described supra, with virus produced by the cell contacted with the candidate anti-viral compound. Efficacy of the candidate anti-viral compound is determined by comparing the expression level of the reporter gene polypeptide by the genetically engineered cell or cell population to that of a control genetically engineered cell or cell population contacted with virus produced by an infected cell not contacted with the candidate anti-viral compound.

DETAILED DESCRIPTION

Figure 1:
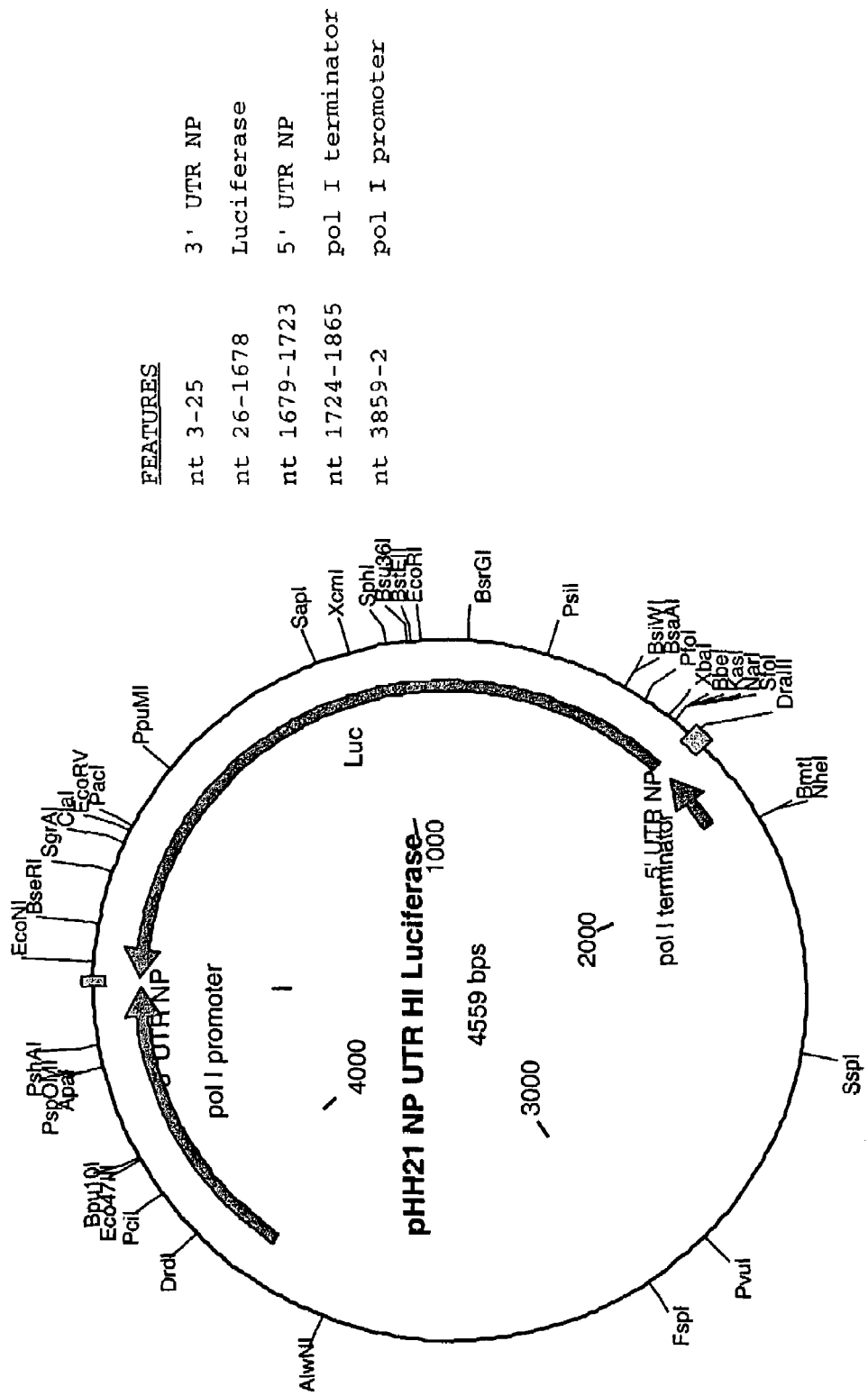
FIG. 1 illustrates a map of plasmid pHH21 NP UTR HI luciferase.

In accordance with the present invention, methods and compositions for detecting the presence, absence, or quantity of segmented negative strand RNA viruses are provided. The invention is based on the inventors' observations that an artificial segment of a segmented negative strand RNA virus harbored by a genetically engineered cell is accessible for formation of a translatable mRNA comprising a reporter gene when the cell further comprises an RNA-dependent RNA polymerase of the segmented negative strand RNA virus. In certain embodiments, the genetically engineered cell comprises the RNA-dependent RNA polymerase by virtue of the cell further comprising one or more nucleic acids encoding polypeptide components of the RNA-dependent RNA polymerase. In some embodiments, the nucleic acids encoding the RNA-dependent RNA polymerase can be viral genomic RNA, for example as provided by infection of the cell with the segmented negative strand RNA virus. Formation of a translatable mRNA comprising the reporter gene can occur even in the absence of a viral nucleocapsid protein in the cell prior to infection. In other embodiments, the nucleic acids encoding the RNA-dependent RNA polymerase can be one or more recombinant DNA molecules. The recombinant DNA molecules can be, for example, a vector or a plurality of vectors, such as, for example, a plasmid or a plurality of plasmids, wherein the vectors comprise cDNAs encoding viral polypeptides that contribute to the viral protein complex comprising the RNA-dependent RNA polymerase. The recombinant DNA molecules can further include one or more vectors comprising a cDNA of a viral nucleocapsid protein. In addition, the invention is based on the inventors' observations that expression of the product of the reporter gene is not detected significantly above background levels in the absence of the RNA-dependent RNA polymerase of the segmented negative strand RNA virus. Because methods of introducing the RNA-dependent RNA polymerase to a host cell include infection of the cell by a segmented negative strand RNA virus, the methods and compositions allow for detecting or diagnosing the presence, absence, or quantity of one or more segmented negative strand RNA viruses in a biological specimen.

The methods and compositions described herein utilize laboratory techniques well known to skilled artisans and which can be found in laboratory manuals such as Sambrook, J., Fritsch, E. F. and Maniatis, T. (1989) Molecular Cloning: A Laboratory Manual, 2nd ed. Cold Spring Harbor Laboratory Press, Cold Spring Harbor, N.Y.

A genetically engineered cell according to the present invention is a vertebrate cell that comprises a recombinant nucleic acid and is susceptible to infection by a segmented negative strand RNA virus to be detected. A segmented negative strand RNA virus can be, for example, an arenavius, a bunyavirus or an orthomyxovirus. An orthomyxovirus can be, for example, an influenza A virus, an influenza B virus, or an influenza C virus. A genetically engineered cell of the invention is susceptible to infection if the genome of the infecting segmented negative strand RNA virus can enter the cell and proceed at least sufficiently far in its replication cycle so that proteins necessary for efficient synthesis of translatable reporter gene mRNA from preformed artificial segment RNA are expressed. Preferably, the infection of the cell with a segmented negative strand RNA virus is fully productive, i.e., progeny virus are produced by an infected cell, and spread from cell to cell. Furthermore, in certain embodiments, a genetically engineered cell is preferably one in which a Pol I promoter (for example, of human or murine origin) functions in order that an artificial segment can be transcribed from a recombinant DNA template. It will be understood by those skilled in the art that a cell line susceptible to infection by a particular segmented negative strand RNA virus can be readily identified by searching the literature for known susceptible cell lines and/or by screening candidate cell lines using well-known procedures requiring only routine experimentation. Non-limiting examples of susceptible cells for segmented negative-strand RNA viruses include the following: human cells such as 293T kidney, LA-4, MRC5, A549, HEp2, 2fTGH, and STAT 1-deficient 2fTGH (U3A), and non-human cells such as baby hamster kidney (BHK), CV-1, Vero, LLC-MK1, monkey primary kidney, and Chinese hamster ovary (CHO). Human 293T cells are preferred for use as the host cell for detecting segmented negative strand RNA viruses that infect mammals, including humans. Susceptible cells are well known in the art and are available from sources such as the American Type Culture Collection, 10801 University Boulevard, Manassas, Va. 20110-2209. A genetically engineered cell of the invention comprising a recombinant DNA molecule as described herein can be a stably transfected or a transiently transfected cell. In certain aspects, the recombinant DNA comprised by a cell can also be comprised by a vector, preferably a plasmid. The vector can also comprise other sequences useful for selection, maintenance, or propagation of a recombinant DNA molecule, such as, for example, a selection marker or an origin of replication, used according to methods well known in the art (e.g., Sambrook et al., supra).

The invention also provides a genetically engineered vertebrate cell comprising an artificial segment of a segmented negative strand RNA virus, or its complement. An artificial segment of the invention is a single-stranded RNA comprising a 5' UTR of a segment of the segmented negative strand RNA virus, an open reading frame of a reporter gene, and a 3' UTR of a segment of a segmented negative strand RNA virus. Preferably, at least one, and preferably both, the 5' UTR and the 3' UTR are from a species of segmented negative strand RNA virus whose presence, absence or quantity is to be detected in a biological specimen. The 5' UTR and the 3' UTR can be from the same or different segments. Preferably, the 5' UTR and the 3' UTR are from the same segment of the segmented negative strand RNA virus whose presence, absence or quantity is to be detected in a biological specimen. Preferably, the open reading frame of a reporter gene of an artificial segment is in the antisense configuration, and the open reading frame of a reporter gene of the complement of an artificial segment is in the sense configuration. In the absence of a viral RNA-dependent RNA polymerase, a host cell is unable to provide a translatable viral mRNA molecule, nor can it synthesize an RNA that is complementary to the segment. However, in the presence of a viral RNA-dependent RNA polymerase, the host cell can provide a translatable viral mRNA molecule, and can also synthesize or replicate both the artificial segment and its complement, in each case using the complementary strand as template. In a host cell comprising a viral RNA-dependent RNA polymerase, the UTRs of an artificial segment can be recognized and serve as transcription initiation sites by the viral RNA-dependent RNA polymerase. In an artificial segment, an open reading frame of a reporter gene is preferably in the anti-sense orientation. Without being bound by theory, it is believed that one or more viral proteins such as a viral RNA-dependent RNA polymerase recognize and bind to the UTRs of the artificial segment. The viral proteins can be introduced to a host cell by a virus upon infection of the host cell. Furthermore, it is believed that by utilizing the artificial segment as template, the RNA-dependent RNA polymerase catalyzes synthesis of an RNA strand complementary to the artificial segment (a "positive-sense" strand), and that a positive-sense strand can be used as template for synthesis of the artificial segment. Furthermore, the RNA-dependent RNA polymerase also utilizes the positive-sense strand as template for synthesis of an artificial mRNA which can be processed into a capped, polyadenylated mRNA (see, e.g., Mikulasova et al., Acta Virol. 44: 273-282, 2000). An mRNA comprising a reporter gene sequence in a sense orientation is available for translation by the cell, resulting in production a polypeptide encoded by the reporter gene. Hence, infection of the cell with a segmented negative strand RNA virus, for example a virus provided by contacting the cell with a diagnostic test sample, leads to expression of viral polypeptides, including those comprising the viral RNA-dependent RNA polymerase, and, hence, expression of the reporter gene polypeptide. In addition, the amount of the polypeptide produced by a genetically engineered cell or a cell population is monotonically related to the amount of the segmented negative strand RNA virus infecting the cell (or a cell population) up to saturating levels of virus, thereby providing a means for quantification of virus levels in a biological specimen. Because no mRNA encoding the reporter gene is synthesized in a host cell in the absence of viral RNA-dependent RNA polymerase, the amount of the reporter gene polypeptide in an uninfected genetically engineered cell of the invention is not significantly greater than that of a control cell not comprising the artificial segment.

The segmented negative strand RNA virus whose presence, absence or quantity is to be detected can be any segmented negative strand RNA virus such as an Arenavirus, an Bunyavirus or an Orthomyxovirus, and is preferably an Orthomyxovirus, and more preferably an influenza virus. The influenza virus can be an influenza A virus, an influenza B virus, or an influenza C virus, and is preferably an influenza A virus or an influenza B virus. Preferably, the artificial segment used to detect the absence, presence, or quantity of a segmented negative strand RNA virus comprises a 5' UTR from a segment of an influenza virus, preferably an influenza A virus, preferably a 5' UTR of the NP segment of an influenza A virus. Preferably, the artificial segment comprises a 3' UTR from a segment of an influenza virus, preferably an influenza A virus, preferably a 3' UTR of the NP segment of an influenza A virus. Preferably, the 5' UTR and the 3' UTR are from the same virus, preferably influenza A virus, and preferably both are from the NP segment of an influenza A virus.

A reporter gene of the invention is any nucleic acid sequence (DNA or RNA) that encodes a detectable product when expressed in a cell. The reporter gene can be, for example, a DNA or RNA sequence comprising an open reading frame such as a cDNA sequence, a genomic DNA sequence, or a synthetic sequence. A reporter gene can also comprise an intron. It is believed that the presence of an intron in a reporter gene nucleic acid sequence can increase expression levels of a polypeptide encoded in a host cell upon stimulation of the cell with viral RNA-dependent RNA polymerase. The reporter gene product is preferably a polypeptide that can be easily assayed or detected in a cell. Assay or detection of a polypeptide can be by any known detection method, such as, for example, immunodetection using an antibody directed against the reporter gene polypeptide; enzyme activity detection using, for example, a fluorogenic, a chromogenic, a chemiluminescent, or a radioactive substrate; or protein fluorescence. Non-limiting examples of a reporter gene product include chloramphenicol acetyl transferase, β-galactosidase, β-glucoronidase, renilla luciferase, firefly luciferase, green fluorescent protein (GFP), and secreted alkaline phosphatase. Preferably, the reporter gene product is a polypeptide that is inherently fluorescent, such as a green fluorescent protein, or is an enzyme for which a chemiluminescent substrate is available, such as firefly luciferase. Preferably, detecting the absence, presence or quantity of the polypeptide comprises detecting the absence, presence, or quantity of an photonic signal emitted by the polypeptide or a substrate thereof. The photonic signal can be, for example, fluorescent light emission from a fluorescent protein such as, for example, a green fluorescent protein, or chemiluminescent light emission from an enzyme for which a chemiluminescent substrate is available, such as, for example, a luciferase such as firefly luciferase or renilla luciferase. Detection or quantification of an optical signal can be by any detection or quantification method known in the art, for example fluorescence microscopy or flow cytometry. The term "green fluorescent protein" includes fluorescent polypeptides such as those comprising naturally occurring wild-type sequences of GFP from *Aequorea victoria* (Chalfie et al., Science, 263: 802-805,1994), as well as fluorescent mutations and derivatives thereof (regardless of color), for example fluorescent proteins described in U.S. Pat. No. 6,054,321 to Tsien et al., U.S. Pat. No. 6,146,826 to Chalfie et al., and U.S. Pat. No. 6,096,865 to Michaels. The term luciferase includes enzymes having naturally occurring chemiluminescent substrates, such as firefly luciferase and renilla luciferase.

In certain embodiments, a genetically engineered cell comprises a recombinant DNA sequence encoding the artificial segment. A genetically engineered cell can be produced by any method known in the art. In some embodiments, a genetically engineered cell can be produced by transfection of the cell with a recombinant DNA of the invention. Transfection can be achieved using methods well known in the art. Preferably, transfection is achieved with the aid of a transfection agent, such as TransIT®-LT1 Transfection Reagent (Mirus Corporation, Madison, Wis.). The recombinant DNA can be provided as an isolated recombinant DNA molecule comprising a recombinant DNA sequence encoding the artificial segment. The isolated recombinant DNA molecule can comprise a vector, such as a recombinant plasmid or recombinant virus. A recombinant virus can be, for example, a recombinant bacteriophage or a recombinant vertebrate virus.

In certain embodiments, the recombinant DNA molecule of these embodiments comprises, in 5' to 3' order, a promoter for a DNA-dependent RNA polymerase, a transcription initiation site for the DNA-dependent RNA polymerase, a DNA sequence encoding an artificial segment or its complement, and a transcription termination site for the DNA-dependent RNA polymerase. The DNA-dependent RNA polymerase used by a genetically engineered cell of the invention for transcription of the recombinant DNA sequence can be a DNA-dependent RNA polymerase endogenous to the cell, or a heterologous DNA-dependent RNA polymerase such as, for example, a DNA-dependent RNA polymerase disclosed in U.S. Pat. No. 6,270,958 to Olivo et al. Preferably, the DNA-dependent RNA polymerase is a DNA-dependent RNA polymerase endogenous to the cell, and is more preferably RNA polymerase I. Hence, the promoter can be a promoter for any RNA polymerase that can function in a vertebrate cell, and is preferably a promoter for an RNA polymerase that is endogenous to the cell, preferably a promoter for RNA polymerase I. The promoter is operably linked to a transcription initiation site, which is, preferably, a Pol I transcription initiation site. The Pol I transcription initiation site can be any sequence that Pol I can recognize for initiating transcription, such as, for example, the sequence 5'-CCAATAA-3'. When this sequence follows a Pol I promoter, transcription is believed to initiate at the nucleotide immediately 3' to this sequence. Because Pol I initiates transcription at a precisely defined sequence, a Pol I transcription initiation site is preferably situated such that a transcript of the DNA comprises an artificial segment in which the 5' terminus coincides exactly or within about 10 nucleotides of the 5' end of the 5' UTR of the cDNA encoding an artificial segment. Preferably, the 5' terminus coincides exactly with the 5' end of the 5' UTR. Alternatively, if the artificial segment is in positive-sense configuration with respect to the promoter, a transcript of the DNA comprises an artificial segment in which the 5' terminus coincides exactly or within about 10 nucleotides of the 5' end of the complement of the 3' UTR of the cDNA encoding an artificial segment. Preferably, the 5' terminus coincides exactly with the 5' end of the 3' UTR. A cDNA encoding an artificial segment comprises a cDNA of a 5' UTR of a segment of a segmented negative strand RNA virus, a DNA sequence of an open reading frame of a reporter gene encoding a polypeptide, and a cDNA of a 3' UTR of a segment of the segmented negative strand RNA virus. The DNA sequence of an open reading frame of a reporter gene can be in either sense or anti-sense configuration with respect to the promoter comprised by the recombinant DNA molecule, and is preferably in an anti-sense configuration with respect to the promoter. The sequence encoding the artificial segment can be in sense or anti-sense orientation with respect to the promoter. Thus, the reporter gene DNA sequence can be in either sense or anti-sense orientation with respect to the promoter. Furthermore, in some embodiments, the reporter gene DNA sequence can also comprise an intron.

The recombinant DNA molecule further comprises a transcription termination site. A "transcription termination site" is defined herein to include any DNA sequence that can be transcribed or processed into an RNA sequence having a defined 3' terminus, such as, for example, a DNA sequence recognized by a DNA-dependent RNA polymerase for transcription termination, a sequence encoding a catalytic RNA sequence such as a self-cleaving ribozyme, or a terminal sequence of a linear DNA. A transcription termination site is preferably a transcription termination site recognized by RNA polymerase I. In preferred embodiments, the Pol I transcription termination site can be delineated by the sequence 5'-GGGGGG-3'. In alternative embodiments, a transcription termination site can comprise a sequence encoding a catalytic RNA sequence, such as a self-cleaving ribozyme. A transcription termination site of the invention is positioned in the DNA sequence such that upon transcription, the 3' terminal of the RNA transcribed from the DNA is exactly at, or within about 10 nucleotides of, the 3' end of the 3' UTR of the artificial segment. In preferred embodiments, upon transcription, the 3' terminal of the RNA transcribed from the DNA is exactly at the 3' end of the 3' UTR. Alternatively, if the artificial segment is in positive-sense configuration with respect to the promoter, a transcription termination site of the invention is positioned in the DNA sequence such that upon transcription, the 3' terminal of the RNA transcribed from the DNA is exactly at, or within about 10 nucleotides of, the 3' end of the complement of the 5' UTR of the complement of an artificial segment. In preferred embodiments, upon transcription, the 3' terminal of the RNA transcribed from the DNA is exactly at the 3' end of the complement of the 5' UTR.

In certain embodiments, the recombinant DNA molecule is a vector such as, for example, a recombinant plasmid or a recombinant virus. Preferably the vector is a recombinant plasmid. Non-limiting examples of plasmids include pHH21NPUTR-luc and pHH21NPUTR-GFP, in which the promoter for the DNA-dependent RNA polymerase is a Pol I promoter, the UTRs are from the NP segment of influenza A virus, and the reporter genes encode firefly luciferase and green fluorescent protein, respectively. Such vectors can be constructed using materials and methods well known to skilled artisans (e.g., Sambrook et al., supra). In non-limiting example, such vectors can be constructed using a plasmid comprising a Pol I promoter, such as plasmid pHH21 (Neumann, G., et al., Proceedings of the National Academy of Sciences USA 96: 9345-9350, 1999; Neumann, G., et al., Virology 202: 477-479, 1994).

Without being bound by theory, it is believed that because of its sequence structure, the recombinant DNA in some embodiments of the invention is transcribed by an RNA polymerase such as Pol I to form an RNA transcript having 5' and 3' terminal sequences that are identical, or nearly identical, to those of a segment or segments of a segmented negative strand virus, thereby forming an artificial segment. Hence, an artificial segment accumulates in the cell prior to infection with a virus comprised by a biological specimen. Unlike methods for detection of nonsegmented viruses, detection of a segmented virus by methods of the present invention does not require the expression in the cell of viral proteins prior or in addition to viral infection. However, expression levels of a reporter polypeptide can be enhanced if the genetically engineered cell further comprises viral proteins such as nucleocapsid proteins. For example, such viral proteins can be provided to a cell through transfection of the cell with one or more plasmids each comprising a promoter for a DNA-dependent RNA polymerase (such as RNA polymerase II) operably linked to a cDNA for a viral protein.

In other embodiments, the invention provides compositions and methods for detecting the presence, absence, or quantity of a first segmented negative strand RNA virus and a second segmented negative strand RNA virus in a biological specimen. A genetically engineered cell of this embodiment comprises two artificial segments or their complements. A first artificial segment comprises a 5' UTR of a first segmented negative strand RNA virus, a first nucleic acid sequence encoding a reporter polypeptide, and a first 3' UTR of the first segmented negative strand RNA virus. A second artificial segment comprises a 5' UTR of a second segmented negative strand RNA virus, a second nucleic acid sequence encoding a reporter polypeptide, and a second 3' UTR of the second segmented negative strand RNA virus. For both the first and the second artificial segments, the nucleic acid sequence encoding a reporter polypeptide can be in sense or anti-sense configurations, and are preferably in anti-sense configurations. A cell in these embodiments can further comprise either a first recombinant DNA molecule and a second recombinant DNA molecule each comprising a promoter for a DNA-dependent RNA polymerase operably linked to sequences for transcription of an artificial segment as described supra. Alternatively, a single recombinant DNA molecule can comprise two promoters for a DNA-dependent RNA polymerase, each promoter operably linked to sequences for transcription of one of two artificial segments as described supra. In these embodiments, the viruses can be any pair of segmented negative strand viruses, such as, in non-limiting example, a pair of viruses selected from an Arenavirus, an Bunyavirus, an influenza A virus, an influenza B virus, and an influenza C virus. Upon contact with a biological specimen comprising two viruses, mRNAs comprising the reporter genes are formed in proportion to the amount of each virus. Accordingly, the reporter genes are expressed in proportions reflecting the viral content of the biological specimen. For example, a genetically engineered cell of this embodiment can comprise a first artificial segment comprising UTRs from influenza A and the second artificial segment comprising UTRs from influenza B, the artificial segments comprising different reporter genes. Upon contact of the cell with a biological sample comprising both influenza A and influenza B viruses, the amounts of the reporter gene polypeptides made by the cell will be proportional to the amount of the viruses in the specimen. Preferably, the polypeptides encoded by the reporter genes of these embodiments are light-emitting polypeptides or are enzymes for which light-emitting substrates are available, and are preferably selected from the group consisting of firefly luciferase, renilla luciferase, and a green fluorescent protein.

In yet other embodiments, the invention provides a method of determining a differential diagnosis between an infection of influenza A virus, influenza B virus, or neither virus in a biological specimen suspected of comprising an influenza virus. The method comprises contacting the biological specimen with a population of genetically engineered cells, wherein a substantial plurality of the genetically engineered cells comprise an artificial segment that comprises at least one UTR of a segment of an influenza A virus, and reporter gene encoding a polypeptide. A "substantial plurality" of genetically engineered cells comprising an artificial segment can be at least about 50%, preferably at least about 75%, more preferably at least about 90% of the cells comprising an artificial segment. The reporter gene is preferably in anti-sense configuration. One or both of the 5' UTR and 3' UTR of the artificial segment of these cells are preferably a UTR of a segment of an influenza A virus, more preferably an NP segment. Expression of the reporter gene polypeptide depends upon the presence in the cell of a viral RNA-dependent RNA polymerase of an influenza virus A virus or an influenza B virus. In preferred embodiments, the polypeptide encoded by the reporter gene is a protein that can be detected by light emission, for example a green fluorescent protein or a luciferase protein. In these embodiments, quantitative measurement of reporter gene expression in the cell population reveals the viral content of the biological specimen: a cell population contacted with a biological specimen comprising influenza A virus produces an amount of reporter gene product substantially greater than that of an uninfected control culture, whereas a cell population contacted with a biological specimen comprising influenza B virus produces an amount of reporter gene product that is slightly greater than that of an uninfected control culture. In some embodiments, quantitative analysis of reporter gene expression can comprise a measurement of reporter gene polypeptide expressed in the cell population as a whole. In other embodiments, quantitative analysis can comprise measuring reporter gene polypeptide levels on a cell-by-cell basis, for example using a reporter gene and flow cytometry or a fluorescence-activated cell sorter. Thus, in some embodiments, samples known to comprise either influenza A virus, influenza B, or neither virus can be used to establish reporter gene expression levels by cultures in response these viruses. These expression levels can provide guidance for determining the type of virus comprised by a biological sample suspected of comprising an influenza virus. For example, the percentage of cells expressing the reporter gene polypeptide will be reflective of percentages measured using control cultures infected with one of the viruses. Thus, for example, a biological specimen for which contact with the cell population leads to expression of the reporter polypeptide in the majority of the cells, for example at least about 80% of the cells or at least about 90% of the cells can be diagnosed as comprising influenza A virus, while a biological specimen for which contact with the cell population leads to expression of the reporter polypeptide in a minority of cells, for example about 10% of the cells, can be diagnosed as comprising influenza B virus. Furthermore, a biological specimen for which contact with the cell population leads to expression of the reporter polypeptide in less than about 3% of the cells can be diagnosed as comprising neither virus.

In another embodiment, the invention provides a kit comprising packaging and an isolated recombinant DNA molecule, the isolated recombinant molecule comprising a reporter gene in which expression in a cell transfected with the molecule depends upon the presence in the cell of a viral RNA of the segmented negative strand virus. In this embodiment, the isolated recombinant DNA molecule comprises, in 5' to 3' order, a promoter for a DNA-dependent RNA polymerase, a transcription initiation site for the DNA-dependent RNA polymerase, a cDNA of a 5' UTR of a segment of a segmented negative strand RNA virus, a DNA sequence of an open reading frame of a reporter gene encoding a polypeptide, a cDNA of a 3' UTR of a segment of the segmented negative strand RNA virus and a transcription termination site for the DNA-dependent RNA polymerase. The DNA sequence of an open reading frame of a reporter gene of this embodiment can be in the sense or anti-sense orientation, and is preferably in the anti-sense orientation. A kit of this embodiment can also comprise a cell or cell population susceptible to infection by a segmented negative strand RNA virus, such as those described supra. The cell or cell population can be a genetically engineered cell transfected with the isolated recombinant DNA molecule. Alternatively, the cell or cell population can be non-transfected. A user of the kit can transfect the cell or cell population with the DNA using standard methods well known to the skilled artisan, then use the transfected cells to measure the presence, absence, or quantity of a segmented negative strand RNA virus. Transfections can be conducted by standard procedures well known to skilled artisans, such as those described in Sambrook et al., supra.

In another embodiment, the invention provides a quantitative screen for an anti-viral drug directed against proliferation or gene expression of a segmented negative strand RNA virus. The virus is preferably an influenza virus such as an influenza A virus. The quantitative screen comprises (a) contacting a candidate anti-viral compound with a genetically engineered cell or cell population that comprises (i) an artificial segment comprising a sequence encoding a reporter gene polypeptide as described supra, and (ii) a protein complex comprising an RNA-dependent RNA polymerase of the segmented negative strand RNA virus, and (b) detecting the quantity of the polypeptide produced by the cell or cell population. In certain embodiments, the protein complex comprising an RNA-dependent RNA polymerase of a segmented negative strand RNA virus can be provided in the cell or cell population by one or more nucleic acids, each nucleic acid encoding at least one polypeptide component of a replication complex of a segmented negative strand RNA virus. In other embodiments, the protein complex can be provided in the cell by infection of the cell with the virus, or by transfection of the cell with viral RNA. Efficacy of a candidate anti-viral compound is determined by comparing the expression level of the reporter gene polypeptide in the cell or cell population contacted with the compound to that of a control cell or cell population not contacted with the compound. The expression level of the reporter gene polypeptide can be determined by measuring the total amount of reporter gene polypeptide expressed by a cell. In some embodiments, expression of the reporter gene polypeptide can be determined by measuring the percentage of cells expressing the reporter gene polypeptide. In non-limiting example, flow cytometry can be used to provide a two dimensional plot of numbers of cells vs. reporter gene polypeptide expression levels when the reporter gene polypeptide is either a GFP or a luciferase. Standard analytical techniques can be used to determine the efficacy of the candidate compound, for example the collected data can be used to determine an effective dose providing a 50% reduction in reporter gene expression ($ED_{50}$) of a candidate compound. This quantitative screen provides rapid results and is simple to execute.

In another embodiment, the invention provides a viral yield assay for an anti-viral drug directed against a segmented negative strand RNA virus. In this embodiment, a first cell (or population of cells) is contacted with a candidate anti-viral compound. The first cell is also infected with the virus. The first cell is of a type that is susceptible to proliferative infection by the virus. Viral production by the cell or cell population is then measured using a production sample comprising a sample of virus (if any) produced by the first cell or cell population following infection and contact with the candidate anti-viral compound. Anti-viral activity of the compound is determined by contacting the production sample with a second cell (or population of cells), wherein the second cell or cell population is a genetically engineered cell or cell population comprising an artificial segment comprising a reporter gene encoding a polypeptide in which expression depends upon the presence in the cell of an RNA-dependent RNA polymerase of the virus, as described supra. A reduction in expression level of the reporter gene (compared to controls) is indicative of anti-viral activity by the candidate anti-viral compound.

The following examples are provided for illustrative purposes only and are not to be interpreted as limiting the scope of the present invention. The examples will permit better understanding of the invention and better perception of its advantages.

EXAMPLE 1

This example illustrates structure and functioning of plasmid pHH21 NP UTR HI luciferase.

This plasmid (FIG. 1) encodes a luciferase ORF flanked by the UTRs of the influenza A/WSN/33 segment 5. In a cell comprising this plasmid, transcription is controlled by an RNA polymerase I promoter and terminator, such that a negative or genomic sense RNA transcript is produced when the plasmid is transcribed by Pol I. In this plasmid, a DNA sequence encoding a luciferase reporter polypeptide replaces the open reading frame of a cDNA of an influenza A virus NP segment comprised by a human RNA polymerase I expression vector (plasmid pHH21; Neumann, G., et al., Proceedings of the National Academy of Sciences USA 96: 9345-9350, 1999; Neumann, G., et al., Virology 202: 477-479, 1994). Nucleotide sequences corresponding to functional regions of the plasmid are indicated. A cell transfected with this plasmid and infected with influenza A virus can express luciferase. Similarly, a cell transfected with this plasmid and further transfected with plasmids encoding viral proteins PA, PB1, PB2, and NP can also express luciferase.

EXAMPLE 2

This example illustrates an influenza A virus detection process.

Figure 2:
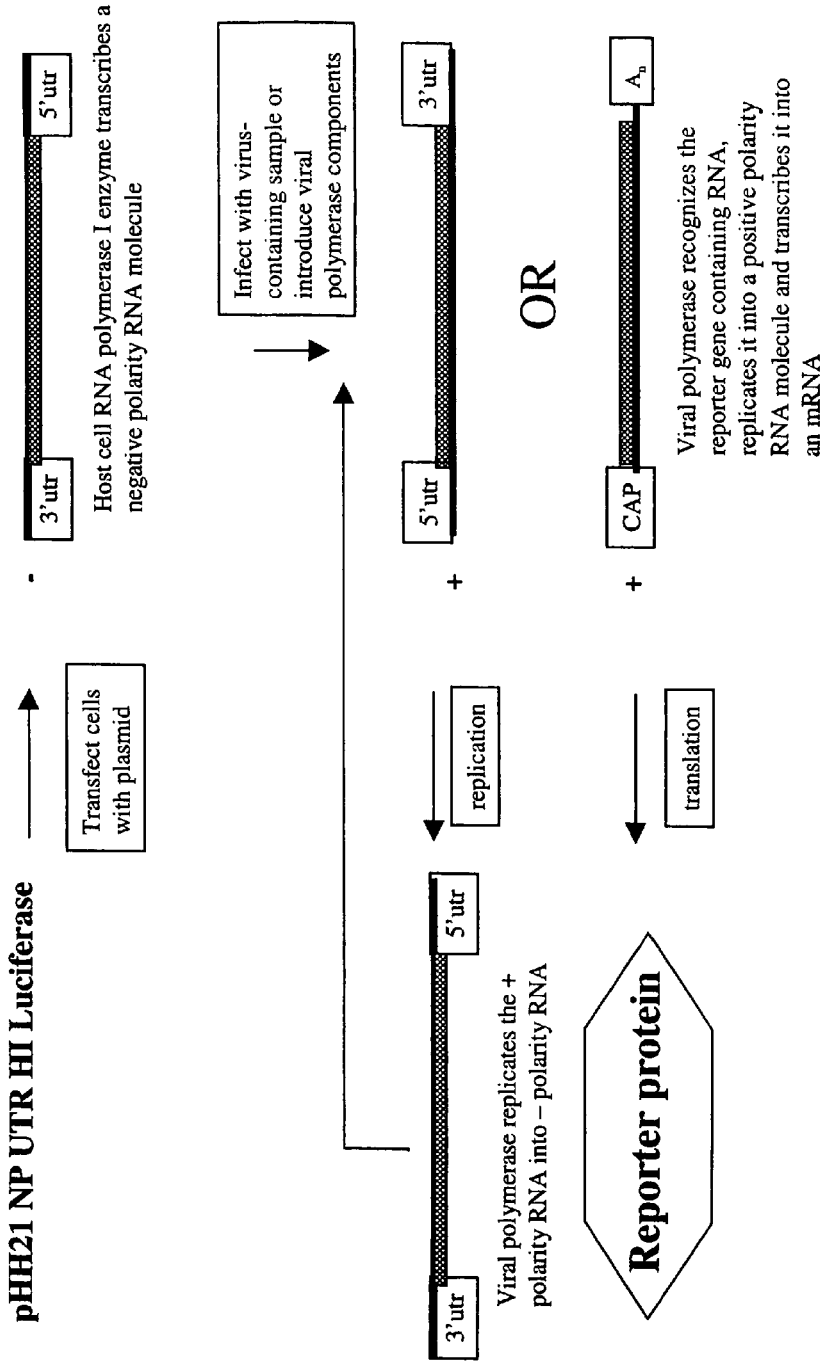
FIG. 2 illustrates influenza A virus detection using an artificial segment.

In this example (FIG. 2), transfected cells produce a negative or genomic sense RNA transcript using the RNA polymerase I enzyme. Upon infection with influenza A virus or expression of the influenza A virus polymerase complex, the transcript is replicated to a full length positive-sense RNA or a 5' capped, 3' polyadenylated mRNA. The positive-sense RNA is replicated to form additional viral, negative-sense RNA while the mRNA is translated by the host cell machinery into the reporter protein. The luciferase reporter polypeptide can be detected and quantified by standard methods known in the art.

EXAMPLE 3

This example illustrates an influenza A virus detection procedure.

Figure 3:
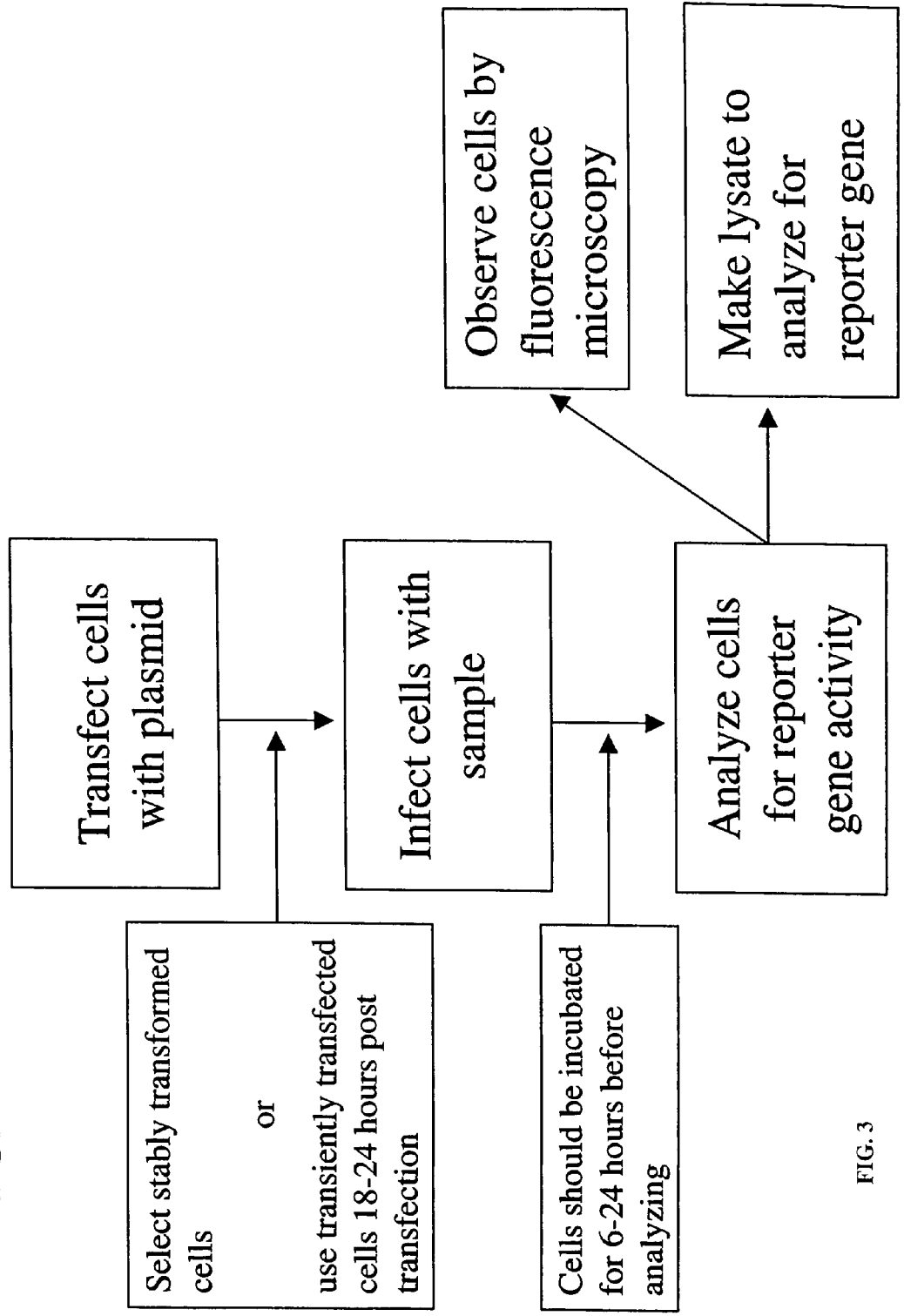
FIG. 3 illustrates a block diagram of an influenza A virus detection procedure.

In this procedure, cells are transfected with the pHH21 luciferase or a similar plasmid (FIG. 3). The cells can then be selected for stably transfected subpopulations or used directly. A biological specimen (e.g., a clinical specimen or a virus sample) is then incubated with the cells for a duration expected to be sufficient for generation of a detectable signal. The incubation time can be at least about six hours. Preferably, the incubation time can be from at least about six hours to about fourteen days, from at least about six hours to about 120 hours, or from at least about six hours to about twenty-four hours. After exposure to the sample, the cells are analyzed for expression of reporter gene polypeptide by standard methods known in the art.

EXAMPLE 4

This example illustrates expression of a reporter gene from an artificial influenza A segment.

Figure 4:
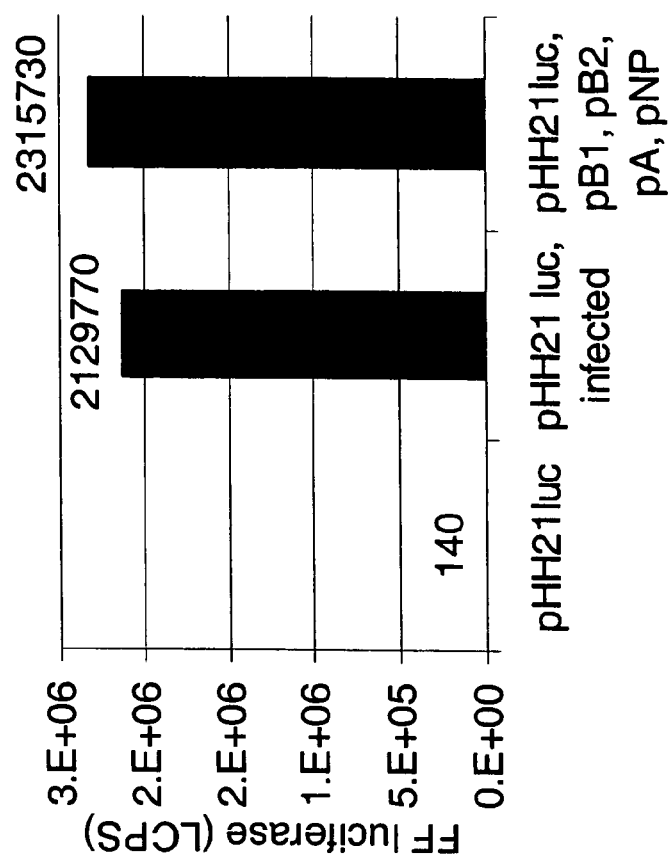
FIG. 4 illustrates firefly luciferase expression by genetically engineered cells comprising an artificial segment comprising UTRs from a segment of an influenza A virus and a luciferase ORF.
Figure 5:
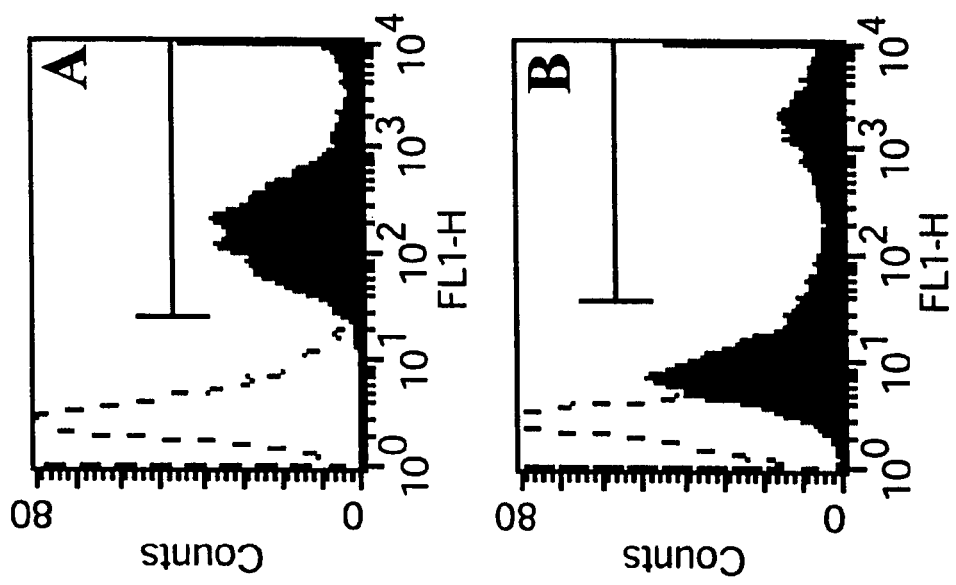
FIG. 5 illustrates green fluorescent protein expression by genetically engineered cells comprising an artificial segment comprising UTRs from a segment of an influenza A virus and a GFP ORF.

In this example, the firefly luciferase gene was cloned in place of the NP open reading frame in the human RNA polymerase I expression vector pHH21 that contains the UTRs from the NP segment The resultant plasmid, pHH21NPUTR-luc, allows for expression of a functional influenza virus artificial segment RNA that can be transcribed by the influenza virus RNA polymerase complex, thereby allowing luciferase expression in the presence of infecting virus. Human 293T cells were transfected with pHH21NPUTR-luc, and were either infected with influenza virus strain WSN/33 at a multiplicity of infection (MOI) of 5, or were co-transfected with expression vectors for the influenza virus replication and nucleocapsid proteins (pPA, pPB1, pPB2, and pNP, encoding viral polypeptides PA, PB1, PB2 and NP, respectively). Forty-two hours after transfection (or 18 hours after infection with influenza virus for cells transfected with pHH21NPUTR-luc alone), the cells were lysed and assayed for firefly luciferase activity using the GLOW kit (Promega, Madison Wis.). Transfection with the plasmids in the absence of infection resulted in a very high signal (>$2\times10^6$ LCPS) with a signal-to-noise of over 16,000 (FIG. 4, lane 3). However, viral infection of cells transfected only with the plasmid comprising an artificial segment (pHH21NPUTR-luc), was also sufficient to promote reporter gene expression (FIG. 4, lane 2).

EXAMPLE 5

This example illustrates GFP reporter genes as indicators of influenza A virus activity.

To facilitate screening for influenza A virus activity using fluorescence-based readouts, a cDNA containing the GFP open reading frame flanked by the UTRs of the NP segment of influenza virus A/WSN/33 was constructed. This cDNA was cloned into the pHH21 vector which drives transcription of the artificial segment, NP UTR-GFP, via the human RNA polymerase I promoter and terminator. 293T cells were transfected with NP UTR-GFP. Twenty-four hours post transfection, the cells were infected with influenza A virus. Eighteen hours after infection, the cells were analyzed for GFP expression. High amounts of GFP were present in 100% of the virus-infected cells (FIG. 5A; solid, filled histogram) whereas mock-infected cells expressed little or no GFP (FIG. 5A; open, dashed-line histogram). These data indicate infection-dependent production of GFP in NP UTR-GFP expressing cells. This infection-dependent method allows for a virus detection system.

To determine whether this reporter gene construct could function in an infection-independent process, 293T cells were transfected with plasmids expressing the influenza ORFs required for RNA replication and transcription (PA, PB1, PB2 and NP); along with pNP-UTR-GFP. A plasmid containing no exogenous ORF was included in the transfection as a control. Among cells transfected with cDNAs encoding all four viral polymerase proteins, GFP was detected in approximately 35% of the cells (FIG. 5B, solid, filled histogram) while cells transfected with only three of the four viral polymerase expression plasmids did not show appreciable expression of GFP (FIG. 5B, open, dashed line histogram). These data indicate that GFP reporter gene activity from NP-UTR-GFP is detectable in an infection-independent assay. Thus, the data in FIG. 3 demonstrates the use of reporter genes flanked by influenza A virus UTRs as tools for quantifying viral RNA-dependent RNA polymerase activity whether the polymerase is delivered by infection or transfection.

EXAMPLE 6

This example illustrates induction of reporter gene expression by influenza A virus and influenza B virus but not influenza C virus.

To determine if the influenza A virus NP-UTR-GFP transcript could be recognized by a polymerase complex of other members of the Orthomyxoviridae, pHH21NPUTR-GFP-transfected cells were infected with influenza A (strain WSN/33), influenza B (strain Yamagata/59), or influenza C (strain Jerusalem/99). Influenza A/WSN/33-infected cells displayed greater than 99% GFP-positive cells while influenza B/Yamagata/59 showed only 9.8% GFP-positive cells. Furthermore, the mean channel fluorescence in GFP-positive influenza A/WSN/33-infected cells was 2963 while the corresponding population in influenza B/Yamagata/59-infected cells had a mean channelfluorescence of only 88. These data indicate that while the GFP reporter is expressed to a high degree in influenza A virus-infected cells, it is only marginally expressed in influenza B virus-infected cells. Both mock-infected and influenza C-infected cultures had 2.5% GFP positive cells, indicating that the reporter was not expressed in influenza C-infected cells. This suggests that NP UTR GFP transcript was neither recognized nor transcribed by the influenza C virus polymerase complex. This assay can be used diagnostically to determine if a biological specimen, for example a blood sample from a human patient displaying symptoms of influenza, comprises influenza A virus, influenza B virus, or neither virus.

As various changes could be made in the above methods and compositions without departing from the scope of the invention, it is intended that all matter contained in the above description be interpreted as illustrative and not in a limiting sense.

All references cited in this specification are hereby incorporated by reference in their entirety. The discussion of the references herein is intended merely to summarize the assertions made by their authors and no admission is made that any reference constitutes prior art relevant to patentability. Applicants reserve the right to challenge the accuracy and pertinency of the cited references.

What is claimed is:

1. A method for detecting the presence, absence, or quantity of a segmented negative strand RNA virus in a biological sample suspected of comprising the virus, the method comprising:

a) providing a genetically engineered vertebrate cell comprising a recombinant RNA molecule that comprises an artificial segment of a segmented negative strand RNA virus or the complement thereof, the artificial segment comprising a 5' untranslated region (UTR) of a segmented negative strand RNA virus, a reporter gene encoding a polypeptide, and a 3' UTR of a segmented negative strand RNA virus, wherein expression of the polypeptide depends upon the presence in the cell of an RNA-dependent RNA polymerase of the virus suspected of being comprised by the sample and wherein the cell lacks at least one nucleocapsid protein of the virus;

b) contacting the cell with a biological sample suspected of comprising a segmented negative strand RNA virus; and c) detecting the absence, presence, or quantity of the polypeptide encoded by the reporter gene, thereby indicating the absence, presence, or quantity, respectively, of the virus suspected of being comprised by the sample.

2. The method according to claim 1, wherein the segmented negative strand RNA virus is selected from the group consisting of influenza A virus, influenza B virus, and influenza C virus.

3. The method according to claim 1, wherein at least one of the 5' UTR and the 3' UTR is a UTR of the virus suspected of being comprised by the biological sample.

4. The method according to claim 3, wherein the artificial segment comprising the 5' UTR comprises the 5' UTR of the NP segment of an influenza A virus.

5. The method according to claim 3, wherein the 3' UTR of the artificial segment comprises the 3' UTR of the NP segment of an influenza A virus.

6. The method according to claim 1, wherein the polypeptide encoded by the reporter gene is selected from the group consisting of chloramphenicol acetyl transferase, β-galactosidase, β-glucuronidase, renilla luciferase, firefly luciferase, a green fluorescent protein, and secreted alkaline phosphatase.

7. The method of claim 6, wherein the polypeptide encoded by the reporter gene is selected from the group consisting of a green fluorescent protein and a firefly luciferase.

8. The method according to claim 1, wherein the detecting the absence, presence, or quantity of the polypeptide encoded by the reporter gene comprises detecting the absence, presence, or quantity of a photonic signal emitted by the polypeptide.

9. The method according to claim 1, wherein the genetically engineered vertebrate cell is selected from the group consisting of a 293T kidney cell, an LA-4 cell, a MRC5 cell, an A549 cell, a CV-1 cell, a Vero cell, a LLC-MK1 cell, a HEp2 cell, a 2fTGH cell, a U3A cell, a BHK cell, a monkey primary kidney cell, and a Chinese hamster ovary cell.

10. A method for detecting the presence, absence, or quantity of a segmented negative strand virus in a biological sample suspected of comprising the segmented negative strand RNA virus, the method comprising:
   a) providing a genetically engineered vertebrate cell comprising a recombinant DNA molecule that comprises in 5' to 3' order:
      a promoter for a DNA-dependent RNA polymerase;
      a transcription initiation site for the DNA-dependent RNA polymerase;
      a DNA sequence encoding an artificial segment comprising a cDNA of a 5' untranslated region (UTR) of a segmented negative strand RNA virus, a reporter gene encoding a polypeptide, and a cDNA of a 3' UTR of a segmented negative strand RNA virus; and
      a transcription termination site,
   wherein said promoter, said transcription initiation site, said artificial segment, and said transcription termination site are operably linked, and wherein expression of the polypeptide depends upon the presence in the cell of an RNA-dependent RNA polymerase of the virus suspected of being comprised by the sample and wherein the cell lacks at least one nucleocapsid protein of the virus;
   b) contacting the cell with a biological specimen suspected of comprising the virus; and
   c) detecting the absence, presence, or quantity of the polypeptide encoded by the reporter gene, thereby indicating the absence, presence, or quantity, respectively, of the virus suspected of being comprised by the sample.

11. The method according to claim 10, wherein the promoter for a DNA-dependent RNA polymerase is a promoter for RNA polymerase I.

12. The method according to claim 10, wherein the transcription initiation site is a transcription initiation site for RNA polymerase I.

13. The method according to claim 10, wherein the DNA sequence encoding an artificial segment is operably linked to the promoter such that a transcript of the artificial segment is in an anti-sense orientation.

14. The method according to claim 10, wherein the DNA encoding an artificial segment is operably linked to the promoter such that a transcript of the artificial segment is in a sense orientation.

15. The method according to claim 10, wherein at least one of the 3' UTR and the 5' UTR is a UTR of the virus suspected of being comprised by the biological sample.

16. The method according to claim 10, wherein the at least one of the 3' UTR and the 5' UTR is a UTR of the NP segment of an influenza A virus.

17. The method according to claim 10, wherein the segmented negative strand virus is a virus selected from the group consisting of influenza A virus, influenza B virus, and influenza C virus.

18. The method according to claim 10, wherein the reporter gene encodes a polypeptide selected from the group consisting of chloramphenicol acetyl transferase, β-galactosidase, β-glucuronidase, renilla luciferase, firefly luciferase, a green fluorescent protein, and secreted alkaline phosphatase.

19. The method of claim 18, wherein the polypeptide is selected from the group consisting of a green fluorescent protein and a firefly luciferase.

20. The method according to claim 10, wherein the transcription termination site is an RNA polymerase I transcription termination site.

21. The method according to claim 10, wherein the transcription termination site comprises a sequence encoding a self-cleaving ribozyme.

22. The method according to claim 10, wherein the genetically engineered vertebrate cell is a stably transfected genetically engineered vertebrate cell.

23. The method according to claim 10, wherein the genetically engineered vertebrate cell is a transiently transfected genetically engineered vertebrate cell.

24. The method according to claim 10, wherein the genetically engineered vertebrate cell is a transfected cell selected from the group consisting of a 293T kidney cell, an LA-4 cell, a MRCS cell, an A549 cell, a CV-1 cell, a Vero cell, a LLC-MK1 cell, a HEp2 cell, a 2fTGH cell, a U3A cell, a BHK cell, a monkey primary kidney cell, and a Chinese hamster ovary cell.

25. The method according to claim 1, wherein said genetically engineered vertebrate cell of step (a) lacks all nucleocapsid proteins of the virus.

26. The method according to claim 1, wherein said genetically engineered vertebrate cell of step (a) lacks at least one viral protein selected from the group consisting of PA, PB1, PB2 and NP.

27. The method according to claim 10, wherein said genetically engineered vertebrate cell of step (a) lacks all nucleocapsid proteins of the virus.

28. The method according to claim 10, wherein said genetically engineered vertebrate cell of step (a) lacks at least one viral protein selected from the group consisting of PA, PB1, PB2 and NP.

* * * * *